US00PP16067P2

(12) United States Plant Patent
Moonen

(10) Patent No.: US PP16,067 P2
(45) Date of Patent: Oct. 25, 2005

(54) ***AGASTACHE* PLANT NAMED 'KIEGAPUR'**

(50) Latin Name: *Agastache mexicana*
Varietal Denomination: Kiegapur

(75) Inventor: Carla Moonen, Enkhuizen (NL)

(73) Assignee: Kieft Bloemzaden B.V., Venhuizen (NL)

( * ) Notice: Subject to any disclaimer, the term of this patent is extended or adjusted under 35 U.S.C. 154(b) by 61 days.

(21) Appl. No.: 10/822,983

(22) Filed: Apr. 13, 2004

(51) Int. Cl.[7] ..... A01H 5/00
(52) U.S. Cl. ..... Plt./263
(58) Field of Search ..... Plt./263

(56) References Cited

PUBLICATIONS

UPOV–Rom 'hit' on 'Kiegapur', GTI Jouve Retrieval software 2004/02.*

* cited by examiner

*Primary Examiner*—Anne Marie Grunberg
(74) *Attorney, Agent, or Firm*—C. A. Whealy

(57) ABSTRACT

A distinct cultivar of *Agastache* plant named 'Kiegapur', characterized by its upright, outwardly spreading and open plant habit; freely basal branching growth habit; numerous purple-colored flowers positioned close together on erect flowering spikes; and good garden performance.

1 Drawing Sheet

Botanical classification/cultivar designation: *Agastache mexicana* cultivar Kiegapur.

BACKGROUND OF THE INVENTION

The present Invention relates to a new and distinct cultivar of *Agastache* plant, botanically known as *Agastache mexicana*, commercially known as Hyssop, and hereinafter referred to by the name 'Kiegapur'.

The new *Agastache* is a product of a planned breeding program conducted by the Inventor in Venhuizen, The Netherlands. The objective of the breeding program is to create new *Agastaches* with improved plant habit and flowering characteristics and attractive flower coloration.

The new *Agastache* originated from a cross-pollination made by the Inventor in 2001, of a proprietary seedling selection of *Agastache mexicana* identified as code number 96(0360-1), not patented, as the female, or seed parent, with a proprietary seedling selection of *Agastache mexicana* identified as code number 97(0024), not patented, as the male, or pollen parent. The new *Agastache* was selected as a single plant from the resulting progency of the cross-pollination by the Inventor in a controlled environment in Venhuizen, The Netherlands.

Asexual reproduction of the new cultivar by cuttings in a controlled environment in Venhuizen, The Netherlands since 2001, has shown that the unique features of this new *Agastache* are stable and reproduced true to type in successive generations.

SUMMARY OF THE INVENTION

Plants of the cultivar Kiegapur have not been observed under all possible environmental conditions. The phenotype may vary somewhat with variations in environment and culture such as temperature and light intensity without, however, any variance in genotype.

The following traits have been repeatedly observed and are determined to be the unique charateristics of 'Kiegapur'.

These characteristics in combination distinquish 'Kiegapur' as a new and distinct cultivar of *Agastache*:

1. Upright, outwardly spreading and open plant habit.
2. Freely basal branching growth habit.
3. Numerous purple-colored flowers positioned close together on erect flowering spikes.
4. Good garden performance.

In side-by-side comparisons conducted in Venhuizen, The Netherlands, plants of the new *Agastache* differed primarily from plants of the female parent selection in flower color as plants of the female parent selection had lilac-colored flowers.

In side-by-side comparisons conducted in Venhuizen, The Netherlands, plants of the new *Agastache* differed from plants of the male parent selection primarily in flower color as plants of the male parent selection had pink-colored flowers.

Plants of the new *Agastache* can be compared to plants of the cultivar Champagne, not patented. In side-by-side comparisons conducted in Venhuizen, The Netherlands, plants of the new *Agastache* and the cultivar Champagne differed in the following characteristics:

1. Plants of the new *Agastache* had brighter green-colored foliage than plants of the cultivar Champagne.
2. Plants of the new *Agastache* and the cultivar Champagne differed in flower color as plants of the cultivar Champagne had pink orange-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Agastache*.

The photograph at the bottom of the sheet comprises a side perspective view of a typical flowering plant of 'Kiegapur'.

The photograph at the top of the sheet comprises a close-up view of a typical inflorescence of 'Kiegapur'.

DETAILED BOTANICAL DESCRIPTION

The aforementioned photographs and following observations and measurements describe plants grown in Lompoc, Calif., under commercial practice during the winter in a polycarbonate-covered greenhouse with day temperatures about 21 to 24° C., night temperatures about 16 to 18° C. and light levels about 5,000 to 9,000 foot-candles. Plants were grown with one rooted cutting per 15.25-cm container for about eleven weeks. In the following description, color references are made to The Royal Horticultural Society Colour Chart except where general terms of ordinary dictionary significance are used.

Botanical classification: *Agastache mexicana* cultivar Kiegapur.

Parentage:

*Female, or seed, parent*.—Proprietary seedling selection of *Agastache mexicana* identified as code number 96(0360-01) not patented.

*Male, or pollen, parent*.—Proprietary seedling selection of *Agastache mexicana* identified as code number 97(0024), not patented.

Propagation:

*Type cutting*.—Vegetative cuttings.

*Time to initiate roots*.—About two weeks at 21° C.

*Time to develop roots*.—About three weeks at 21° C.

*Root description*.—Fine; white in color.

*Rooting habit*.—Freely branching.

Plant description:

*Form*.—Upright, outwardly spreading and open plant habit. Freely basal branching with about seven primary lateral branches and numerous secondary branches. Moderately vigorous growth habit.

*Plant height*.—About 29 cm.

*Plant diameter*.—About 30 cm.

*Lateral branches*.—Length: About 30 cm. Diameter: About 3 mm. Internode length: About 5 cm. Strength: Moderately strong. Texture: Smooth, glabrous. Color: 146A.

*Foliage description*.—Arrangement: Opposite, simple. Length: About 3 cm. Width: About 2 cm. Shape: Elliptic. Apex: Acute. Base: Attenuate. Margin: When developing, entire; fully expanded, sparsely serrate. Aspect: Mostly flat. Texture, upper and lower surfaces: Smooth, glabrous. Venation pattern: Pinnate, arcuate. petiole length: About 7 mm. Petiole diameter: About 1 mm. Color: Developing and fully expanded foliage, upper surface: 147A. Developing and fully expanded foliage, lower surface: 147B. Venation, upper and lower surfaces: 146B. Petiole, upper and lower surfaces: 146B.

Flower description:

*Flower type and habit*.—Numerous single bilabiate flowers arranged in verticillasters arranged in axillary spikes. Individual flowers face mostly outward. Freely flowering with about 42 flowers and flower buds per spike. Flowers not persistent.

*Natural flowering season*.—Plants flower throughout the summer, flowering continuous during this period.

*Flower longevity on the plant*.—About five to seven days.

*Fragrance*.—Very faint; spicy sweet.

*Inflorescence length*.—About 3.5 cm.

*Inflorescence width*.—About 5 cm.

*Flowers*.—Appearance: Zygomorphic; bilabiate. Length: About 3.2 cm. Diameter: About 7 mm.

*Flower buds*.—Length: About 1 cm. Diameter: About 2 mm. Shape: Elongated oblong. Color: 71B.

*Corolla*.—Petal arrangement/appearance: Bilabiate; five petals, upper two petals fused and lower three petals fused, all five petals fused at base into a tubular structure. Petal length: Upper petals, lobes: About 3 mm. Lower petals, lobes: About 6 mm. Petal width: Upper petals, lobes: About 2 mm. Lower petals, lobes: About 6 mm. Petal apex: Broadly acute. Petal margin: Entire. Petal texture, upper and lower surfaces: Finely pubescent: sanity. Petal color: When opening, upper and lower surfaces: 77B. Fully opened, upper surface: 77B. Fully opened, lower surface: Slightly lighter than 77B.

*Calyx*.—Quantity/arrangement: One single calyx tube per flower; five fused sepals. Length: About 1 cm. Diameter: About 2.5 mm. Shape: Tubular. Apex: Acute. Texture, upper and lower surfaces: Pubescent. Color, upper and lower surfaces: Darker than 195A and tinged with 185D.

*Peduncles*.—Length: About 8.5 cm. Diameter: Less than 1 mm. Strength: Strong. Angle: About 45° from vertical. Texture: Pubescent. Color: 143B.

*Pedicels*.—Length: About 2 mm. Diameter: Less than 1 mm. Strength: Moderately strong. Angle: About 45 to 60° from vertical. Texture: Pubescent. Color: 143B.

*Reproductive organs*.—Stamens: Quantity per flower. Four. Anther shape: Oval. Anther length: Less than 1 mm. Anther color: 90A. Pollen amount: Scarce. Pollen color: 155A. Pistils: Quantity per flower: One. Pistil length: About 3.3 cm. Style length: About 3.1 mm. Style color: 78B. Stigma shape: Bi-parted. Stigma color: 78A. Ovary color: 145B.

*Seed/fruit*. —Seed nor fruit production has not been observed.

Disease/pest resistance: Plants of the new *Agastache* have not been noted to be resistant to pathogens or pests common to *Agastache*.

Garden performance: Plants of the new *Agastache* have been observed to have good garden performance and to be tolerant to rain, wind and temperatures ranging from 5 to 35° C.

It is claimed:

1. A new and distinct cultivar of *Agastache* plant named 'Kiegapur', as illustrated and described.

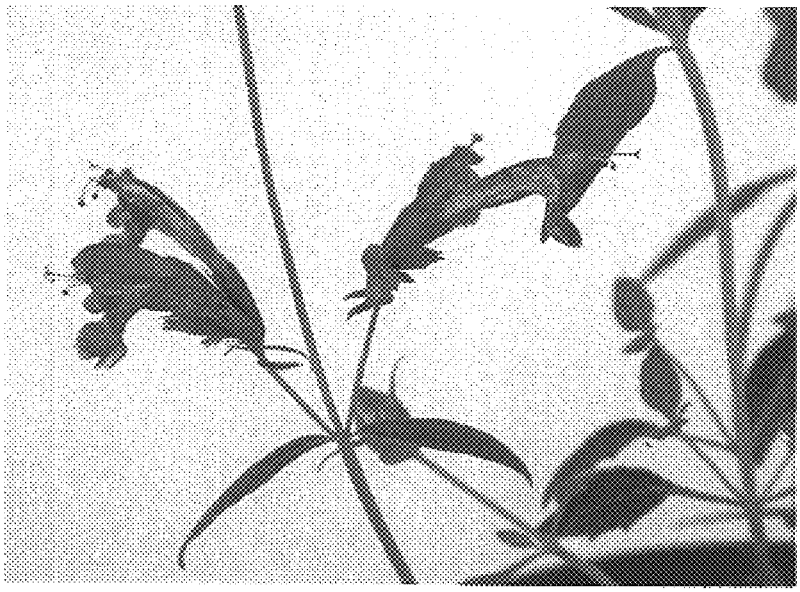
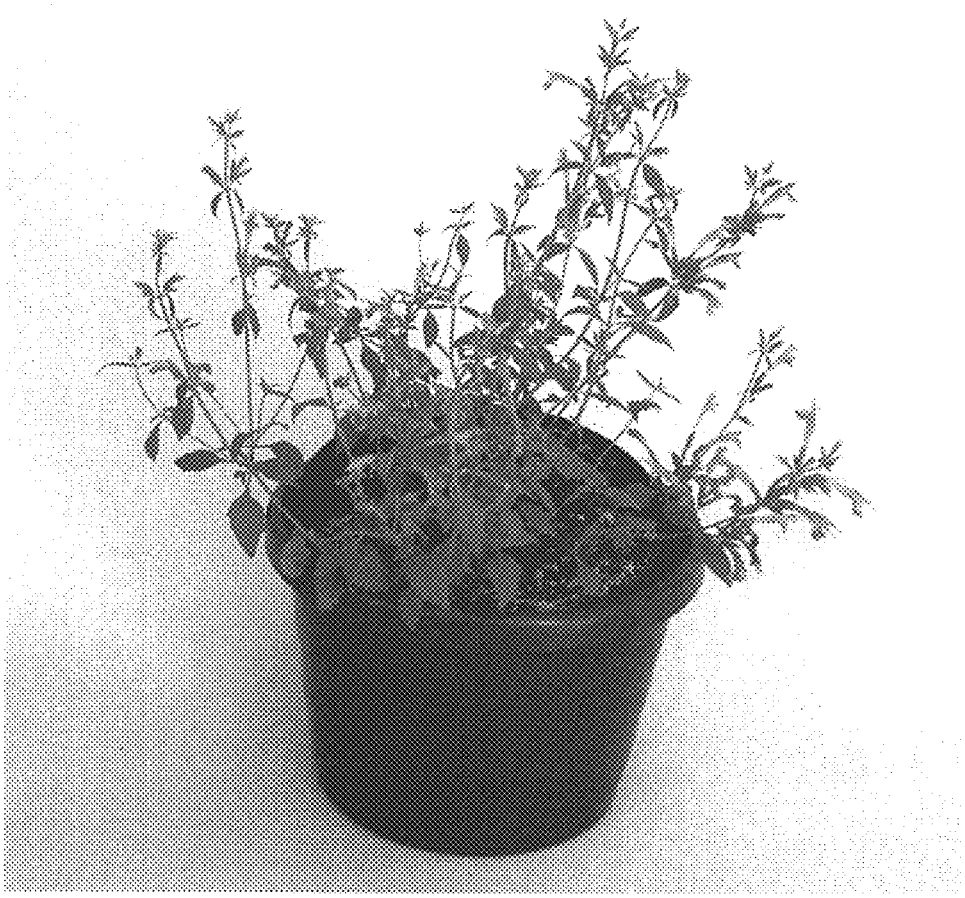

* * * * *